(12) United States Patent
Yorozuya et al.

(10) Patent No.: US 7,902,383 B2
(45) Date of Patent: Mar. 8, 2011

(54) PRODUCTION METHOD OF HETEROCYCLIC MERCAPTO COMPOUND

(75) Inventors: Shinichi Yorozuya, Kawasaki (JP); Hidemasa Aoki, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 102 days.

(21) Appl. No.: 12/302,226

(22) PCT Filed: May 28, 2007

(86) PCT No.: PCT/JP2007/061231
§ 371 (c)(1),
(2), (4) Date: Nov. 24, 2008

(87) PCT Pub. No.: WO2007/139215
PCT Pub. Date: Dec. 6, 2007

(65) Prior Publication Data
US 2009/0171095 A1  Jul. 2, 2009

(30) Foreign Application Priority Data

May 29, 2006  (JP) .................................. 2006-148586

(51) Int. Cl.
*C07D 307/00* (2006.01)
*C07D 309/30* (2006.01)
*C07D 213/69* (2006.01)
*C07D 207/00* (2006.01)

(52) U.S. Cl. .......... 549/313; 549/292; 546/296; 548/551

(58) Field of Classification Search .................. 549/313, 549/292; 548/551; 546/296
See application file for complete search history.

(56) References Cited

U.S. PATENT DOCUMENTS 3,328,415 A * 6/1967 Surrey et al. .................. 548/186

FOREIGN PATENT DOCUMENTS

| JP | 04-103584 A | 4/1992 |
| JP | 2000-169445 A | 6/2000 |
| JP | 2002-543069 A2 | 12/2002 |
| WO | WO 00/64882 A2 | 11/2000 |

OTHER PUBLICATIONS

European Patent Office, Patent Abstracts of Japan Publication No. 2000169445.*
Fuchs et al. Arkiv For Kemi Band 26 nr 10, Chemistry Scheme, compound XII; IDS filed Aug. 28, 2009, NPL Cite No. 1).*
Georg Fuchs; "Some 2- or 3-mercapto substituted γ-lactones"; Arkiv for Kemi Band 26 nr 10 (1966), pp. 111-116.
Miyauchi et al., "Synthesis and Structure-Activity Relationships of a Novel Oral Carbapenem, CS-834," The Journal of Antibiotics, vol. 50, No. 5, May 1997, pp. 429-439.

* cited by examiner

Primary Examiner — Nizal S Chandrakumar
(74) Attorney, Agent, or Firm — Sughrue Mion, PLLC

(57) ABSTRACT

A method of the invention industrially produces heterocyclic mercapto compounds useful as raw materials or intermediates in the synthesis of medicaments or pesticides, or as permanent wave agent, with a high yield and high productivity using easily available starting materials. A heterocyclic mercapto compound represented by Formula (1) (wherein X represents any structure of —O—, —S—, —NH—, and —NR$^1$—; R$^1$ represents any of an alkyl group, alkoxy group and alkoxyalkyl group each having 1 to 6 carbon atoms; Y represents an oxygen atom, a sulfur atom or —NR$^2$—; R$^2$ represents a hydrogen atom or alkyl group having 1 to 6 carbon atoms; and Z$^1$ represents a divalent organic residue having at least one mercapto group) is produced by reacting a metal sulfide or a metal hydrosulfide with a compound represented by Formula (2) (wherein X and Y are as defined in Formula (1); and Z$^2$ represents a divalent organic residue having at least one halogen group) in the presence of a solvent at a pH of 7.0 to 11.0.

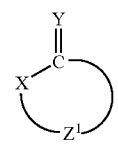

(1)

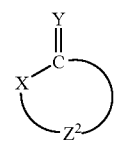

(2)

15 Claims, No Drawings

PRODUCTION METHOD OF HETEROCYCLIC MERCAPTO COMPOUND

FIELD OF THE INVENTION

The present invention relates to a method for effectively producing a heterocyclic mercapto compound.

BACKGROUND OF THE INVENTION

Conventionally, mercapto compounds have been widely used as raw materials for synthesizing various medicines and pesticides. Especially, the usefulness of heterocyclic mercapto compounds as medicines is highly appreciated (Patent Document 2), but there are industrial problems with respect to the yields and the raw materials in the production thereof.

More specifically, the heterocyclic mercapto compounds are produced by reacting heterocyclic compounds with alkali salts of thiocarboxylic acids or with thiourea. Prior to the reaction, leaving substituents (for example, halogen group, mesyl group, tosyl group) other than target substituents of substitution reaction are protected and, after the reaction, the protected substituents are deprotected (Non-patent Document 1, Patent Documents 1 to 3). However, the production method using thiourea gives low yields of the objective compounds and is not industrially practical (Patent Document 1). Further, the alkali salts of thiocarboxylic acids are expensive, and therefore the production of the heterocyclic mercapto compounds therewith is unsatisfactory with respect to the industrial practicability (Non-patent Document 1, Patent Documents 1 to 3). In view of industrial practicability and costs, it is desirable that expensive sulfurizing agents represented by the alkali salts of thiocarboxylic acids be replaced by inexpensive sulfurizing agents such as metal sulfides and metal hydrosulfides. In the background art, however, use of sodium hydrosulfide as the sulfurizing agent has resulted in a low yield (Non-patent Document 1).

[Patent Document 1] U.S. Pat. No. 3,328,415

[Patent Document 2] JP-A-2002-543069

[Patent Document 3] JP-A-H04-103584

[Nonpatent Document 1] GEORG FUCH, "ARKIV FOR KEMI", 26 (1966) (pages 111 to 116)

DISCLOSURE OF THE INVENTION

An object of the present invention is to provide a method for industrially producing heterocyclic mercapto compounds useful as raw materials or intermediates in the synthesis of medicines or pesticides and permanent wave agents, with a high yield and high productivity using easily available raw materials.

The present inventors have made extensive and intensive studies and have developed a method by which heterocyclic mercapto compounds can be easily produced from inexpensive and easily available raw materials. Thus, the present invention has been completed. That is, the present invention relates to the following [1] to [16].

[1] A method for producing heterocyclic mercapto compounds represented by Formula (1):

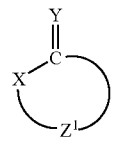

(1)

wherein X represents any structure of —O—, —S—, —NH—, and —NR$^1$—; R$^1$ represents any of an alkyl group, alkoxy group and alkoxyalkyl group each having 1 to 6 carbon atoms; Y represents an oxygen atom, a sulfur atom or —NR$^2$—; R$^2$ represents a hydrogen atom or alkyl group having 1 to 6 carbon atoms; and Z$^1$ represents a divalent organic residue having at least one mercapto group, the method comprising reacting a metal sulfide or a metal hydrosulfide with a compound represented by Formula (2) in the presence of a solvent at a pH of 7.0 to 11.0:

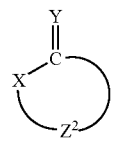

(2)

wherein X and Y are as defined in Formula (1); and Z$^2$ represents a divalent organic residue having at least one halogen group.

[2] The method for producing heterocyclic mercapto compounds according to [1], wherein Z$^1$ in Formula (1) is a divalent organic residue having one mercapto group and the mercapto group is directly bound to the carbon atom at the 2-position of the heterocyclic mercapto compound, and Z$^2$ in Formula (2) is a divalent organic residue having one halogen group and the halogen group is directly bound to the carbon atom at the 2-position of the compound represented by Formula (2).

[3] The method for producing heterocyclic mercapto compounds according to [1], wherein the heterocyclic mercapto compound represented by Formula (1) is a heterocyclic mercapto compound selected from the group consisting of 2-mercapto-4-butyrolactone (2-mercapto-4-butanolide), 2-mercapto-4-methyl-4-butyrolactone, 2-mercapto-4-ethyl-4-butyrolactone, 2-mercapto-4-butyrothiolactone, 2-mercapto-4-butyrolactam, N-methoxy-2-mercapto-4-butyrolactam, N-ethoxy-2-mercapto-4-butyrolactam, N-methyl-2-mercapto-4-butyrolactam, N-ethyl-2-mercapto-4-butyrolactam, N-(2-methoxy)ethyl-2-mercapto-4-butyrolactam, N-(2-ethoxy)ethyl-2-mercapto-4-butyrolactam, 2-mercapto-5-valerolactone, 2-mercapto-5-valerolactam, N-methyl-2-mercapto-5-valerolactam, N-ethyl-2-mercapto-5-valerolactam, N-(2-methoxy)ethyl-2-mercapto-5-valerolactam, N-(2-ethoxy)ethyl-2-mercapto-5-valerolactam, and 2-mercapto-6-hexanolactam.

[4] The method for producing heterocyclic mercapto compounds according to any one of [1] to [3], wherein the metal sulfide is an alkali metal sulfide, an alkaline earth metal sulfide or a mixture thereof.

[5] The method for producing heterocyclic mercapto compounds according to any one of [1] to [3], wherein the metal sulfide is at least one compound selected from the group consisting of sodium sulfide, potassium sulfide, calcium sulfide and magnesium sulfide.

[6] The method for producing heterocyclic mercapto compounds according to any one of [1] to [3], wherein the metal hydrosulfide is sodium hydrosulfide or potassium hydrosulfide.

[7] The method for producing heterocyclic mercapto compounds according to any one of [1] to [6], wherein the solvent is a mixed solvent of water and an organic solvent in which the water:organic solvent weight ratio is 1:0.1-10.

[8] The method for producing heterocyclic mercapto compounds according to [7], wherein the organic solvent is one or more solvents selected from the group consisting of methanol, N-methylpyrrolidone, acetone, 1,4-dioxane, 1,2-dimethoxyethane and N,N-dimethylformamide.

[9] The method for producing heterocyclic mercapto compounds according to any one of [1] to [8], wherein the pH is maintained in the aforementioned range by adding an inorganic acid or an inorganic alkali to the reaction solution from the start of the reaction to the completion of the reaction.

[10] The method for producing heterocyclic mercapto compounds according to any one of [1] to [9], wherein the reaction is performed at not more than 40° C.

[11] The method for producing heterocyclic mercapto compounds according to any one of [1] to [10], wherein the reaction is performed by dissolving or dispersing the metal sulfide or the metal hydrosulfide in the solvent and adding the compound represented by Formula (2) to the resultant solution or slurry while controlling the temperature of the solution or slurry in the range of −20 to 40° C.

[12] The method for producing heterocyclic mercapto compounds according to any one of [1] to [11], wherein the reaction is performed by dissolving or dispersing the metal sulfide or the metal hydrosulfide in the solvent; adjusting the pH of the resultant solution or slurry in the range of 7.5 to 11.0; and adding the compound represented by Formula (2) to the solution or slurry.

[13] The method for producing heterocyclic mercapto compounds according to [12], wherein the pH of the solution or slurry of the metal sulfide or the metal hydrosulfide is achieved by adding an inorganic acid to the solution or slurry while controlling the temperature of the solution or slurry at not more than 40° C.

[14] The method for producing heterocyclic mercapto compounds according to any one of [1] to [13], wherein the equivalent ratio of the compound represented by Formula (2) to the metal sulfide or the metal hydrosulfide is 1:0.8-5.0.

[15] The method for producing heterocyclic mercapto compound according to any one of [1] to [14], further comprising adjusting the pH of the reaction solution in the range of 2.0 to 6.0 after the completion of the reaction.

[16] The method for producing heterocyclic mercapto compounds according to [15], wherein the pH of the reaction solution after the reaction is achieved by adding an inorganic acid thereto after the completion of the reaction.

According to the production method of the present invention, heterocyclic mercapto compounds represented by Formula (1) can be obtained with a high yield and high productivity. Further, since the production method of the present invention does not involve steps for protecting substituents with protective groups and deprotecting such protected substituents, the heterocyclic mercapto compound can be produced through a reduced number of steps when compared to conventional methods. Moreover, the production method of the present invention is applicable to halogenoheterocyclic compounds having various substituents, and thus is extremely useful as an industrial production method.

PREFERRED EMBODIMENTS OF THE INVENTION

Hereinafter, the present invention will be more specifically described.

<Heterocyclic Mercapto Compounds>

The heterocyclic mercapto compounds obtainable by the production method of the present invention are represented by Formula (1):

wherein X represents any structure of —O—, —S—, —NH— or —NR$^1$—; R$^1$ represents any of an alkyl group, alkoxy group and alkoxyalkyl group each having 1 to 6 carbon atoms; Y represents an oxygen atom, a sulfur atom or —NR$^2$—; R$^2$ represents a hydrogen atom or alkyl group having 1 to 6 carbon atoms; and Z$^1$ represents a divalent organic residue having at least one mercapto group.

In Formula (1), X represents any structure of —O—, —S—, —NH— or —NR$^1$—. R$^1$ represents any of an alkyl group, alkoxy group or alkoxyalkyl group each having 1 to 6 carbon atoms. Among them, alkyl groups, alkoxy groups and alkoxyalkyl groups each having 1 to 4 carbon atoms are preferred, and methyl group, ethyl group, methoxy group, ethoxy group, methoxyethyl group and ethoxyethyl group are more preferred from the viewpoints of industrial availability of raw materials and handling.

In Formula (1), Y represents an oxygen atom, a sulfur atom or —NR$^2$—. R$^2$ represents a hydrogen atom or alkyl group having 1 to 6 carbon atoms. Among them, a hydrogen atom, methyl group and ethyl group are preferred as R$^2$ from the viewpoints of industrial availability of raw materials and handling. Among above listed, an oxygen atom is more preferred from the viewpoints of industrial availability of raw material and handling.

In Formula (1), Z$^1$ represents a divalent organic residue having at least one mercapto group (—SH). Z$^1$ may has one or more mercapto groups, and more preferably has one mercapto group. The organic residue Z$^1$ is preferably what one or more mercapto groups are bound to a hydrocarbon group, and may have a branched chain or a side chain. Examples of the side chains include alkyl groups and alkenyl groups.

Preferred examples of such divalent organic residues include alkylene groups to which at least one mercapto group is bound. The mercapto group may be bound to any position of the alkylene group without limitation. The mercapto group may be bound to the alkylene group either directly or via another alkylene group or the like (for example, the mercaptoethyl group may be bound to a carbon atom of the alkylene group).

However, when the mercapto group is directly bound to the alkylene group, it is less mobile than when it is bound via any group. When using the compound of Formula (1) as a permanent wave agent, the reactivity of the mercapto group of it to the cystine bonds in hair is enhanced. Thus, it is preferable that the mercapto group is directly bound to the alkylene group.

When the mercapto group is bound directly to the alkylene group, it is preferable that the mercapto group is bound to the carbon atom at the 2-position of the heterocyclic mercapto compound represented by Formula (1) from the viewpoint of easy substitution of the halogen group at the position in the raw material compound with the mercapto group. The "carbon atom at the 2-position" refers to the first carbon atom from the carbon atom to which Y is bonded, on the side opposite to the substituent —X— in Formula (1). This definition also applies to the "carbon atom at the 2-position" in Formula (2). The alkylene groups desirably have 2 to 8 carbon atoms, preferably 3 to 7 carbon atoms in the main chain. Examples of the side chains which may be present in the alkylene groups include alkyl groups and alkenyl groups having 1 to 3 carbon atoms.

Examples of the compounds represented by Formula (1) which are producible by the production method of the present invention include 2-mercapto-3-propiolactone, 2-mercapto-2-methyl-3-propiolactone, 2-mercapto-3-methyl-3-propiolactone, 2-mercapto-3-ethyl-3-propiolactone, 2-mercapto-2,3-dimethyl-3-propiolactone, 2-mercapto-3-propiolactam, 2-mercapto-2-methyl-3-propiolactam, 2-mercapto-3-methyl-3-propiolactam, 2-mercapto-3-ethyl-3-propiolactam, 2-mercapto-2,3-dimethyl-3-propiolactam, 2-mercapto-3-propiothiolactone, 2-mercapto-2-methyl-3-propiothiolactone, 2-mercapto-3-methyl-3-propiothiolactone, 2-mercapto-3-ethyl-3-propiothiolactone, 2-mercapto-2,3-dimethyl-3-propiothiolactone, 3-mercapto-4-butyrolactone, 2,3-dimercapto-4-butyrolactone, 2,4-dimercapto-4-butyrolactone, 3,4-dimercapto-4-butyrolactone, 3-mercapto-4-butyrothiolactone, 3-mercapto-4-butyrolactam, 2,3-dimercapto-4-butyrolactam, 2,4-dimercapto-4-butyrolactam, 3,4-dimercapto-4-butyrolactam, 2-mercapto-4-butyrolactone (otherwise referred to 2-mercapto-4-butanolide), 2-mercapto-2-methyl-4,4-dimethyl-4-butyrolactone, 2-mercapto-3-(2-propenyl)-4-butyrolactone, 2-mercapto-4-methyl-4-butyrolactone, 2-mercapto-2-methyl-4-butyrolactone, 2-mercapto-3-methyl-4-butyrolactone, 2-mercapto-4-methyl-4-butyrolactone, 2-mercapto-3,4-dimethyl-4-butyrolactone, 2-mercapto-2-ethyl-4-butyrolactone, 2-mercapto-3-ethyl-4-butyrolactone, 2-mercapto-4-ethyl-4-butyrolactone, 2-mercapto-4-butyrothiolactone, 2-mercapto-2-methyl-4-butyrothiolactone, 2-mercapto-3-methyl-4-butyrothiolactone, 2-mercapto-4-methyl-4-butyrothiolactone, 2-mercapto-3,4-dimethyl-4-butyrothiolactone, 2-mercapto-2-ethyl-4-butyrothiolactone, 2-mercapto-3-ethyl-4-butyrothiolactone, 2-mercapto-4-ethyl-4-butyrothiolactone, 2-mercapto-4-butyrolactam, 2-mercapto-2-methyl-4-butyrolactam, 2-mercapto-3-methyl-4-butyrolactam, 2-mercapto-4-methyl-4-butyrolactam, 2-mercapto-3,4-dimethyl-4-butyrolactam, 2-mercapto-2-ethyl-4-butyrolactam, 2-mercapto-3-ethyl-4-butyrolactam, 2-mercapto-4-ethyl-4-butyrolactam, 3-mercapto-5-valerolactone, 4-mercapto-5-valerolactone, 2,3-dimercapto-5-valerolactone, 2,4-dimercapto-5-valerolactone, 2,5-dimercapto-5-valerolactone, 3,4-dimercapto-5-valerolactone, 3-mercapto-5-valerothiolactone, 3-mercapto-5-valerolactam, 4-mercapto-5-valerolactam, 2,3-dimercapto-5-valerolactam, 2,4-dimercapto-5-valerolactam, 2,5-dimercapto-5-valerolactam, 2-mercapto-5-valerolactone, 2-mercapto-2-methyl-5-valerolactone, 2-mercapto-3-methyl-5-valerolactone, 2-mercapto-4-methyl-5-valerolactone, 2-mercapto-5-methyl-5-valerolactone, 2-mercapto-2-ethyl-5-valerolactone, 2-mercapto-3-ethyl-5-valerolactone, 2-mercapto-4-ethyl-5-valerolactone, 2-mercapto-5-ethyl-5-valerolactone, 2-mercapto-5-valerolactam, 2-mercapto-2-methyl-5-valerolactam, 2-mercapto-3-methyl-5-valerolactam, 2-mercapto-4-methyl-5-valerolactam, 2-mercapto-5-methyl-5-valerolactam, 2-mercapto-2-ethyl-5-valerolactam, 2-mercapto-3-ethyl-5-valerolactam, 2-mercapto-4-ethyl-5-valerolactam, 2-mercapto-5-ethyl-5-valerolactam, 2-mercapto-5-valerothiolactone, 2-mercapto-2-methyl-5-valerothiolactone, 2-mercapto-3-methyl-5-valerothiolactone, 2-mercapto-4-methyl-5-valerothiolactone, 2-mercapto-5-methyl-5-valerothiolactone, 2-mercapto-2-ethyl-5-valerothiolactone, 2-mercapto-3-ethyl-5-valerothiolactone, 2-mercapto-4-ethyl-5-valerothiolactone, 2-mercapto-5-ethyl-5-valerothiolactone, 3-mercapto-6-hexanolactone, 4-mercapto-6-hexanolactone, 5-mercapto-6-hexanolactone, 2,3-dimercapto-6-hexanolactone, 2,4-dimercapto-6-hexanolactone, 2,5-dimercapto-6-hexanolactone, 3-mercapto-6-hexanolactam, 4-mercapto-6-hexanolactam, 5-mercapto-6-hexanolactam, 2,3-dimercapto-6-hexanolactam, 2,4-dimercapto-6-hexanolactam, 2,5-dimercapto-6-hexanolactam, 2-mercapto-6-hexanolactone, 2-mercapto-2-methyl-6-hexanolactone, 2-mercapto-3-methyl-6-hexanolactone, 2-mercapto-4-methyl-6-hexanolactone, 2-mercapto-5-methyl-6-hexanolactone, 2-mercapto-6-methyl-6-hexanolactone, 2-mercapto-6-hexanolactam, 2-mercapto-2-methyl-6-hexanolactam, 2-mercapto-3-methyl-6-hexanolactam, 2-mercapto-4-methyl-6-hexanolactam, 2-mercapto-5-methyl-6-hexanolactam, 2-mercapto-6-methyl-6-hexanolactam, 2-mercapto-6-hexanothiolactone, 2-mercapto-2-methyl-6-hexanothiolactone, 2-mercapto-3-methyl-6-hexanothiolactone, 2-mercapto-4-methyl-6-hexanothiolactone, 2-mercapto-5-methyl-6-hexanothiolactone, 2-mercapto-6-methyl-6-hexanothiolactone, 2-mercapto-7-heptanolactone, 2-mercapto-7-heptanothiolactone, 2-mercapto-7-heptanolactam, 2-mercapto-8-octanolactone, 2-mercapto-8-octanothiolactone, 2-mercapto-8-octanolactam, 2-mercapto-9-nonalactone, 2-mercapto-9-nonathiolactone, 2-mercapto-9-nonalactam, and N-alkyl derivatives of these lactams, (for example, N-methyl or N-ethyl derivatives), N-alkoxy derivatives (for example, N-methoxy or N-ethoxy derivatives) and N-alkoxyalkyl derivatives (for example, N-(2-methoxy)ethyl or N-(2-ethoxy)ethyl derivatives).

Among them, the production method of the present invention is suitably applied to the industrial production of 3-mercapto-4-butyrolactone, 2,3-dimercapto-4-butyrolactone, 2,4-dimercapto-4-butyrolactone, 3-mercapto-4-butyrolactam, 2,3-dimercapto-4-butyrolactam, 2,4-dimercapto-4-butyrolactam, 2-mercapto-4-butyrolactone (2-mercapto-4-butanolide), 2-mercapto-4-methyl-4-butyrolactone, 2-mercapto-4-ethyl-4-butyrolactone, 2-mercapto-4-butyrothiolactone, 2-mercapto-4-butyrolactam, N-methoxy-2-mercapto-4-butyrolactam, N-ethoxy-2-mercapto-4-butyrolactam, N-methyl-2-mercapto-4-butyrolactam, N-ethyl-2-mercapto-4-butyrolactam, N-(2-methoxy)ethyl-2-mercapto-4-butyrolactam, N-(2-ethoxy)ethyl-2-mercapto-4-butyrolactam, 2,3-dimercapto-5-valerolactone, 2,4-dimercapto-5-valerolactone, 2,5-dimercapto-5-valerolactone, 3-mercapto-5-valerolactam, 4-mercapto-5-valerolactam, 2,3-dimercapto-5-valerolactam, 2,4-dimercapto-5-valerolactam, 2,5-dimercapto-5-valerolactam, 2-mercapto-5-valerolactone, 2-mercapto-5-valerolactam, N-methyl-2-mercapto-5-valerolactam, N-ethyl-2-mercapto-5-valerolactam, N-(2-methoxy)ethyl-2-mercapto-5-valerolactam, N-(2-ethoxy)ethyl-2-mercapto-5-valerolactam, and 2-mercapto-6-hexanolactam.

Further, among them, the production method of the present invention is more suitably applied to the industrial production of 2-mercapto-4-butyrolactone (2-mercapto-4-butanolide), 2-mercapto-4-methyl-4-butyrolactone, 2-mercapto-4-ethyl-4-butyrolactone, 2-mercapto-4-butyrothiolactone, 2-mercapto-4-butyrolactam, N-methoxy-2-mercapto-4-butyrolactam, N-ethoxy-2-mercapto-4-butyrolactam, N-methyl-2-mercapto-4-butyrolactam, N-ethyl-2-mercapto-4-butyrolactam, N-(2-methoxy)ethyl-2-mercapto-4-butyrolactam, N-(2-ethoxy)ethyl-2-mercapto-4-butyrolactam, 2-mercapto-5-valerolactone, 2-mercapto-5-valerolactam, N-methyl-2-mercapto-5-valerolactam, N-ethyl-2-mercapto-5-valerolactam, N-(2-methoxy)ethyl-2-mercapto-5-valerolactam, N-(2-ethoxy)ethyl-2-mercapto-5-valerolactam, and 2-mercapto-6-hexanolactam.

<Halogenoheterocyclic Compound>

In the production method of the present invention, the halogenoheterocyclic compound used as a raw material for producing the heterocyclic mercapto compound is represented by Formula (2):

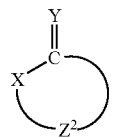

(2)

wherein X and Y are as defined in Formula (1); and $Z^2$ represents a divalent organic residue having at least one halogen group.

The halogenoheterocyclic compound represented by Formula (2) is reacted with a metal sulfide or a metal hydrosulfide to form the heterocyclic mercapto compound represented by Formula (1). Hence, X and Y in Formula (2) are the same as X and Y in the objective compound of Formula (1), respectively.

In Formula (2), $Z^2$ is different from $Z^1$ in Formula (1) and represents a divalent organic residue having at least one halogen group (any of —F, —Cl, —Br, —I and —At in the present invention). The halogen group of $Z^2$ is substituted in the reaction of the halogenoheterocyclic compound with the metal sulfide or the metal hydrosulfide, and consequently the mercapto group is introduced in the heterocyclic compound as shown in Formula (1). Therefore, the number and position of the halogen group(s) correspond to those of the mercapto group(s) of $Z^1$ in Formula (1), and $Z^2$ and $Z^1$ are different from each other only in whether they have the halogen group or the mercapto group. In other words, $Z^2$ except the halogen group is the same as $Z^1$ except the mercapto group.

Therefore, the compound represented by Formula (2) may be appropriately selected so that substituting the halogen group with the mercapto group will produce the objective compound represented by Formula (1). For example, when 2-mercapto-4-butyrolactone is to be produced, the compound represented by Formula (2) may be selected from any of 2-chloro-4-butyrolactone, 2-bromo-4-butyrolactone and 2-iodo-4-butyrolactone. Also, when 2,3-dimercapto-5-valerolactam is to be produced, the compound represented by Formula (2) may be selected from any of 2,3-dichloro-5-valerolactam, 2,3-dibromo-5-valerolactam, 2,3-diiodo-5-valerolactam.

Of the halogen groups, —Br is preferred from the viewpoints of reactivity and availability.

The halogenoheterocyclic compounds represented by Formula (2) are commercially available or may be produced by known methods. For example, the halogenoheterocyclic compounds represented by Formula (2) may be synthesized from commercially available lactone derivatives, thiolactone derivatives or cyclic ketone derivatives by any of the methods described in U.S. Pat. No. 4,247,468, "J. Med. Chem. 1987. 30. 1995-1998", "Tetrahedron Asymmetry 2003. 14. 2587-2594", "Tetrahedron Letters 2005. 46. 3041-3044", and the like.

<Metal Sulfide or Metal Hydrosulfide>

According to the production method of the present invention, the objective heterocyclic mercapto compound (represented by Formula (1)) may be produced by the reaction of the corresponding halogenoheterocyclic compound (represented by Formula (2)) with the metal sulfide or the metal hydrosulfide.

Examples of the metal sulfides include alkali metal sulfides and alkaline earth metal sulfides, and preferred examples include sodium sulfide, potassium sulfide, magnesium sulfide and calcium sulfide. Among them, sodium sulfide and potassium sulfide are more preferred since they are inexpensive and industrially easily available.

Examples of the metal hydrosulfides include alkali metal hydrosulfides. Sodium hydrosulfide and potassium hydrosulfide are preferred since they are inexpensive and industrially easily available.

<Solvent>

Examples of the solvents used for the reaction of the compound of Formula (2) with the metal sulfide or the metal hydrosulfide include water; monoalcohols, such as methanol, ethanol and isopropanol; polyhydric alcohols, such as propylene glycol; ketones, such as acetone and methylethyl ketone; ethers, such as 1,4-dioxane, 1,2-dimethoxyethane, methyl-tert-butyl ether (MTBE), tetrahydrofuran (THF) and diethyl ether; esters, such as ethyl acetate and butyl acetate; N,N-dimethylformamide (DMF); and N-methylpyrrolidone. These solvents are used singly or in combination of two or more kinds. Among them, in view of the reaction yield and the separation of by-products derived from solvent, it is more preferable to use one or more solvents selected from the group of water, methanol, acetone, 1,4-dioxane, 1,2-dimethoxyethane, MTBE, THF, diethyl ether, DMF and N-methylpyrrolidone.

The smaller the amount of the solvent used is, the more easily a side reaction takes place, possibly resulting in a reduced yield of the heterocyclic mercapto compound represented by Formula (1). Although increasing the amount of the solvent suppresses a side reaction and improves the yield of the heterocyclic mercapto compound represented by Formula (1), it also dilutes the concentration of the reaction solution and the productivity can be lowered. Therefore, the amount of the solvent is preferably determined balancing the yield with the productivity. Specifically, the solvent may be used in an amount of 100 to 2000 parts by mass relative to 100 parts by mass of the halogenoheterocyclic compound represented by Formula (2).

When two or more of the above solvents are used in combination, a mixed solvent of water and the organic solvent is preferred. From the viewpoint of improving the yield of the objective compound, water is preferably used in combination with one or more organic solvents selected from the group of methanol, N-methylpyrrolidone, acetone, 1,4-dioxane, 1,2-dimethoxyethane, THF and N,N-dimethylformamide, and is more preferably used in combination with 1,2-dimethoxyethane.

The mixing ratio of water to the organic solvent (weight ratio of water:organic solvent) is preferably 1:0.1-10, more preferably 1:0.1-7.0, still more preferably 1:0.1-5.0.

<pH During the Reaction>

The reaction of the halogenoheterocyclic compound represented by Formula (2) with the metal sulfide or the metal hydrosulfide is suitably performed by bringing the halogenoheterocyclic compound and the metal sulfide or the metal hydrosulfide into contact with each other in the presence of the solvent. Preferably, the metal sulfide or the metal hydrosulfide is dissolved or dispersed in the solvent and the halogenoheterocyclic compound is brought into contact with the resultant solution or slurry.

The solution or slurry of the metal sulfide or the metal hydrosulfide has a pH of around 14 without pH adjustment. However, it is important that during the reaction of the halogenoheterocyclic compound with the metal sulfide or the metal hydrosulfide, the pH of the reaction solution is maintained at 7.0 to 11.0 and the reaction is performed under this pH range. The pH of the reaction solution is preferably 7.0 to 10.0, more preferably 7.0 to 9.5. When the pH is less than 7.0, the conversion of the raw material is not increased and the yield tends to be low. When the pH is more than 11.0, the produced objective compound is decomposed by a side reaction and the yield tends to be low.

The pH of the reaction solution may be measured using a commercially available pH meter. The pH measurement may be performed at the temperature of the reaction solution as it is, without the need of changing the temperature of the reaction solution. In other words, in the present invention, the pH of the reaction solution is measured at the temperature as it is during the reaction.

The pH of the reaction solution may be adjusted by any of the following:

(i) An acid is added beforehand to the solution or slurry of the metal sulfide or the metal hydrosulfide in expectation of pH change of the reaction solution in the reaction of the halogenoheterocyclic compound with the metal sulfide or the metal hydrosulfide, by which the pH of the solution or slurry is adjusted before the reaction.

(ii) The reaction is performed while an acid or an alkali is added to the reaction solution.

(iii) The operations (i) and (ii) are worked together.

When the solution or slurry of the metal sulfide or the metal hydrosulfide is pH-adjusted beforehand, it is preferred that the pH is adjusted such that the pH of the reaction solution is in the aforementioned range during and after the addition of the halogenoheterocyclic compound.

In other words, the pH is desirably adjusted in expectation of a pH of the reaction solution being lowered during the reaction. More specifically, the pH of the solution or slurry of the metal sulfide or the metal hydrosulfide is suitably adjusted to 7.5 to 11.0, preferably 8.0 to 10.0.

This preliminary pH adjustment permits the pH of the reaction solution to be in the range of 7.0 to 11.0 during the reaction, and consequently the heterocyclic mercapto compound represented by Formula (1) is produced with a high yield.

Acids used for the pH adjustment, include inorganic acids and organic acids, with the inorganic acids (mineral acids) being preferable from the viewpoint of no organic by-products generated. Of the inorganic acids, hydrochloric acid, sulfuric acid and nitric acid which are industrially easily available are more preferable. In this case, hydrochloric acid, sulfuric acid and nitric acid may be used singly or in combination of two or more kinds.

When the pH is adjusted before the reaction, the temperature of the solution or slurry of the metal sulfide or the metal hydrosulfide is preferably maintained at 40° C. or less, more preferably 25° C. or less, still more preferably 15° C. or less during the pH adjustment. The lower limit of the temperature depends on the type of the used solvent and is not particularly limited. In general, the temperature is suitably maintained at not less than −20° C. In this case, the measurement of the pH may be performed at that temperature.

When the pH of the reaction solution is adjusted to 7.0 to 11.0 during the reaction, the pH fluctuation is read using a pH meter in the reaction solution, and an acid or an alkali is added appropriately to maintain the pH within the above-mentioned range.

Inorganic acids and organic acids may be used as aforementioned acids, with the inorganic acids (mineral acids) being preferable from the viewpoint of no organic by-products generated. Of the inorganic acids, hydrochloric acid, sulfuric acid and nitric acid which are industrially easily available are more preferable. In this case, hydrochloric acid, sulfuric acid and nitric acid may be used singly or in combination of two or more kinds.

Suitable alkalis for the pH adjustment include inorganic alkalis which are generally used in the industry. Preferable examples of the alkalis include aqueous solutions of sodium hydroxide, potassium hydroxide, calcium hydroxide, sodium hydrosulfide, sodium sulfide, potassium sulfide and potassium hydrosulfide.

During the pH adjustment, a hydrogen sulfide gas is generated by the neutralization. In order that the hydrogen sulfide gas is prevented from being released out of the reaction system, that the total amount of acid required for the pH adjustment is suppressed and that the yield in the main reaction is improved, it is preferred to use a closed reactor.

<Reaction Operation>

The method of the addition of the halogenoheterocyclic compound represented by Formula (2) to the solution or slurry of the metal sulfide or the metal hydrosulfide is illustrated. When the halogenoheterocyclic compound is liquid at normal temperature, such as 2-halogeno-4-butyrolactone, 2-halogeno-4-thiolactone, 2-halogeno-4-ethyl-4-butyrolactone or 2-halogeno-4-methyl-4-butyrolactone, the halogenoheterocyclic compound may be added after being diluted with a solvent or may be added without dilution. In order to suppress a side reaction due to a localized concentration gradient, the halogenoheterocyclic compound is preferably added after being diluted with a solvent. For a similar reason, the halogenoheterocyclic compound which is solid at normal temperature is preferably added after being diluted with a solvent. Preferred examples of the solvents used for the dilution include the above-mentioned organic solvents used for the reaction, and one or more of the organic solvents may be used. It is advisable that the halogenoheterocyclic compound is dissolved in the organic solvent and the resultant solution is added to the solution or slurry of the metal sulfide or the metal hydrosulfide.

The temperature at which the halogenoheterocyclic compound represented by Formula (2) is added to the solution or slurry of the metal sulfide or the metal hydrosulfide greatly affects the yield of the objective heterocyclic mercapto compound. Accordingly, it is preferable that the solution or slurry of the metal sulfide or the metal hydrosulfide is cooled beforehand, and the halogenoheterocyclic compound represented by Formula (2) is added thereto while cooling the reaction solution during the reaction. Herein, the temperature of the reaction solution is usually 40° C. or less, preferably 25° C. or less, more preferably 15° C. or less, still more preferably 5° C.

or less. Although the lower limit of the temperature is not particularly limited, the temperature is suitably not less than −20° C. in view of the productivity of the objective compound.

It is desirable that the reaction system is maintained at a temperature of not more than 40° C. throughout the operations from the above-mentioned addition of the raw material to the completion of the reaction of the halogenoheterocyclic compound represented by Formula (2) with the metal sulfide or the metal hydrosulfide. The reaction of the halogenoheterocyclic compound represented by Formula (2) with the solution or slurry of the metal sulfide or the metal hydrosulfide preferably takes place at a pressure of 0.09 to 0.50 MPa, more preferably 0.10 to 0.30 MPa. When the pressure is less than 0.09 MPa, the selectivity of the objective compound tends to be low. On the other hand, when the pressure is more than 0.50 MPa, a special reactor is required, which is not suitable for the industrial production.

In the above-mentioned reaction, the equivalent ratio of the halogenoheterocyclic compound represented by Formula (2) to the metal sulfide or the metal hydrosulfide (halogenoheterocyclic compound:metal sulfide or metal hydrosulfide) is preferably 1:0.8-5.0, more preferably 1:1.0-5.0. When the equivalent ratio of the metal sulfide or the metal hydrosulfide to the halogenoheterocyclic compound is less than the lower limit of the above-mentioned value, the yield of the objective heterocyclic mercapto compound represented by Formula (1) may decrease. Although the equivalent ratio of the metal sulfide or the metal hydrosulfide to the halogenoheterocyclic compound being more than 5.0 leads to a high reaction yield, the cost for the disposal of the excessive metal sulfide or metal hydrosulfide is increased, and the pH adjustment of the reaction solution requires a large amount of acid to lower the concentration of the reaction solution, often resulting in deteriorated productivity and low industrial value of the production method.

The reaction solution after the reaction contains the heterocyclic mercapto compound represented by Formula (1) and a thiolate anion thereof. The reaction solution after the reaction has a neutral to alkaline, at which the objective heterocyclic mercapto compound is easily oxidized. Among the heterocyclic mercapto compounds represented by Formula (1), those having a lactone skeleton are more likely to be hydrolyzed.

In order to suppress the reduction of the yield due to the oxidation, it is preferable that an acid is added to the reaction solution after the reaction to adjust the pH more acidic, followed by recovering and purifying operations. Herein, the preferable range of the pH is 2.0 to 6.0.

The acids to be added to the reaction solution after the reaction for pH adjustment include general-purpose inorganic acids and organic acids, with the inorganic acids (mineral acids) being preferable from the viewpoint of no organic by-products generated. Of the inorganic acids, hydrochloric acid, sulfuric acid and nitric acid which are industrially easily available are more preferable. In this case, hydrochloric acid, sulfuric acid and nitric acid may be used singly or in combination of two or more kinds.

During the pH adjustment, it is advisable to add the acid while keeping the temperature of the reaction solution at not more than 25° C. in order to avoid hydrolysis in a localized low pH region. The temperature is preferably kept at not more than 15° C., more preferably not more than 5° C. When the temperature exceeds 25° C., hydrolysis is likely to occur. The lower limit of the temperature is not particularly limited as long as the pH adjustment can be performed without the reaction solution being frozen.

Next, the operations for recovering and purifying the objective heterocyclic mercapto compound are described.

After the reaction solution is pH adjusted after the reaction as described above, an organic solvent which is not compatible with the reaction solution is added to the reaction solution and thereby the organic phase which includes the heterocyclic mercapto compound represented by Formula (1) is extracted.

Examples of the organic solvents used for the extraction include diethyl ether, MTBE, isopropyl ether, toluene, dichloromethane, 1,2-dichloroethane, chloroform, ethyl acetate, butyl acetate, hexanol and octanol. One or more of these solvents may be suitably used. From the viewpoints of safety and easy industrial handling, one or more selected from the group of MTBE, chloroform, ethyl acetate and butyl acetate may be suitably used.

Depending on the type and amount of the used solvent, the amount of the metal sulfide or the metal hydrosulfide used and the like in the reaction, inorganic salts may be deposited in the reaction solution after the reaction. In this case, it is desirable that such inorganic salts are removed by centrifugal separation or suction filtration before the extraction operation. It is advisable to wash a cake in a centrifugal separator or on a suction filtration funnel with the organic solvent used for the extraction.

Next, the organic solvent in the extracted organic phase is distilled away. It is preferable that the temperature of the distillation solution during the distillation of the organic solvent in the extracted organic phase is 100° C. or less, preferably 70° C. or less. Depending on the boiling point of the organic solvent used for the extraction, the solvent may be distilled under a reduced pressure.

Evaporating the organic solvent used for the extraction results in a solution which contains the heterocyclic mercapto compound represented by Formula (1). The heterocyclic mercapto compound may be separated and purified directly by column chromatography. When the compound of the Formula (1) is liquid, it may be purified by distillation. When the compound is purified by distillation, it is preferable that the distillation is performed under a reduced pressure which is controlled so that the liquid temperature will be maintained at not more than 200° C., whereby the thermal decomposition of the objective heterocyclic mercapto compound is prevented. Particularly preferably, the reduced pressure is controlled so that the liquid temperature is maintained at not more than 150° C. When the objective compound is a crystallizable compound, it may be purified by recrystallization.

EXAMPLES

Hereinafter, the present invention will be more specifically described referring to the following Examples which should not be construed as limiting the scope of the present invention.

In the following Examples, unless otherwise specified, "%" means "% by mass".

In the following Examples, the high performance liquid chromatography analysis (hereinafter, abbreviated as "HPLC") was performed under the following conditions.

Column: Shodex N,N-814, manufactured by SHOWA DENKO K.K.; having length of 20 cm and inner diameter of 0.5 cm Column temperature: 40° C.

Eluent: 0.1% $H_3PO_4$, 8 mM-$KH_2PO_4$

Flow rate: 1.5 mL/min

Detection: RI, UV (detecting wavelength: 210 nm)

Also in the following Examples, the pH was measured using the following pH meter.

pH meter: Digital pH controller, trade name: FD-02; manufactured by TGK pH meter electrode: electrode for pH controller, trade name: CE-108C; manufactured by TGK Example 1

Production of 2-mercapto-4-butyrolactone 49 g (0.6 mol) of 70% sodium hydrosulfide (manufactured by JUNSEI CHEMICAL Co., Ltd.) were dissolved in a mixture of 34 g of 1,2-dimethoxyethane (Guaranteed Reagent; manufactured by JUNSEI CHEMICAL CO., LTD.) and 34 g of purified water (which had been distilled and passed through an ion exchange filter) at room temperature. While the resultant solution was cooled with ice (to 10° C. or less) and under normal pressure (about 0.10 MPa), 18 g of hydrochloric acid (GUARANTEED REAGENT, 35% to 37%; manufactured by JUNSEI CHEMICAL Co., Ltd.) were added with stirring the solution to adjust the pH of the solution to 8.9. While the solution was maintained at a temperature of 10° C. or less, 34 g (0.2 mol) of 2-bromo-4-butyrolactone (manufactured by Tokyo Chemical Industry Co., Ltd.) were added dropwise into the solution over approximately 20 minutes. The reaction solution after the completion of the dropwise addition was stirred for 2 minutes. The pH of the reaction solution was within the range of 7.5 to 8.9 from when the dropwise addition of 2-bromo-4-butyrolactone was initiated to the stirring after the dropwise addition was completed.

Thereafter, while the solution was cooled at 10° C. or less, 24 g of hydrochloric acid were added to the solution over approximately 5 minutes to adjust the pH of the solution to 4.0. An inorganic salt precipitated in the solution was removed by suction filtration, and 20 g of ethyl acetate (GUARANTEED REAGENT; manufactured by JUNSEI CHEMICAL Co., Ltd.) were added to the resultant filtrate to extract the organic phase. The resultant aqueous phase was reextracted with 34 g of ethyl acetate. These extracted organic phases were combined. The organic phase was concentrated and purified by distillation under a reduced pressure to give 19 g of 2-mercapto-4-butyrolactone (having a boiling point of 94° C./0.3 kPa; with a yield of 78%).

Example 2

Production of 2-mercapto-4-methyl-4-butyrolactone

The procedures of Example 1 were repeated except that instead of 2-bromo-4-butyrolactone, 36 g (0.2 mol) of 2-bromo-4-methyl-4-butyrolactone (manufactured by SIGMA-ALDRICH Corporation) were used. Consequently, 20 g of 2-mercapto-4-methyl-4-butyrolactone (having a boiling point of 73° C./0.4 kPa; with a yield of 77%) were synthesized. The pH of the reaction solution was within the range of 7.4 to 8.9 from when the dropwise addition of 2-bromo-4-methyl-4-butyrolactone was initiated to the stirring after the dropwise addition was completed.

Example 3

Production of 2-mercapto-4-ethyl-4-butyrolactone (1) Production of 2-bromo-4-ethyl-4-butyrolactone To 46 g (0.4 mol) of 4-ethyl-4-butyrolactone (manufactured by SIGMA-ALDRICH Corporation), 2 g (0.07 mol) of 90% phosphorus tribromide (manufactured by Wako Pure Chemical Industries Co., Ltd.) were added at room temperature and the resultant mixture was stirred for 10 minutes. The reaction solution was heated up to 100° C., and 64 g (0.4 mol) of bromine (manufactured by JUNSEI CHEMICAL Co., Ltd.) were added dropwise thereinto through a dropping funnel over one hour. After the completion of the dropwise addition, the reaction solution was stirred at 100° C. for one hour.

The reaction solution after the reaction was cooled to room temperature, and 100 g of water were gradually added thereto and the resultant mixture was stirred for 10 minutes. Further, the mixture was extracted by adding 200 g of ethyl acetate thereto. The aqueous phase obtained by separating the organic phase was reextracted with 90 g of ethyl acetate.

These extracted organic phases were combined and the resultant organic phase was dried by anhydrous sodium sulfate (manufactured by JUNSEI CHEMICAL Co., Ltd.). The organic phase from which the sodium sulfate was filtered off was concentrated and distilled under a reduced pressure to give 50 g of 2-bromo-4-ethyl-4-butyrolactone (having a boiling point of 104° C./0.4 kPa; with a yield of 65%).

(2) Production of 2-mercapto-4-ethyl-4-butyrolactone

In substantially the same manner as in Example 1 except that 39 g (0.2 mol) of the above 2-bromo-4-ethyl-4-butyrolactone were used instead of 2-bromo-4-butyrolactone, the reaction was performed and the reaction solution after the reaction was subjected to the pH adjustment, suction-filtration and extraction operations in the same manner as in Example 1, followed by the distillation-purification of the objective compound to obtain 22 g of 2-mercapto-4-ethyl-4-butyrolactone (having a boiling point of 91° C./0.4 kPa; with a yield of 75%). The pH of the reaction solution was within the range of 7.6 to 8.9 from when the dropwise addition of 2-bromo-4-ethyl-4-butyrolactone was initiated to the stirring after the dropwise addition was completed.

Example 4

Production of 2-mercapto-4-butyrothiolactone (1) Production of 2-bromo-4-butyrothiolactone 100 g (0.98 mol) of 4-butyrothiolactone (manufactured by SIGMA-ALDRICH Corporation) were dissolved in 90 g of ethyl acetate (manufactured by JUNSEI CHEMICAL Co., Ltd.) and the resultant solution was heated up to 63° C. Into the solution, 180 g (1.1 mol) of bromine (manufactured by JUNSEI CHEMICAL Co., Ltd.) were added dropwise through a dropping funnel over 15 minutes. After the completion of the dropwise addition, the reaction solution was stirred at 63° C. for 24 hours.

After the reaction solution after the completion of the reaction was cooled to room temperature, 500 g of water were gradually added thereto and the resultant mixture was stirred for 10 minutes. Further, the mixture was extracted by adding 1000 g of ethyl acetate thereto.

The aqueous phase obtained by separating the organic phase was reextracted with 900 g of ethyl acetate.

These extracted organic phases were combined and the resultant organic phase was dried by anhydrous sodium sulfate (manufactured by JUNSEI CHEMICAL Co., Ltd.). The organic phase from which the sodium sulfate was filtered off was concentrated and distilled under a reduced pressure to give 66 g of 2-bromo-4-butyrothiolactone (having a boiling point of 62° C./0.2 kPa; with a yield of 37%).

(2) Production of 2-mercapto-4-butyrothiolactone

In substantially the same manner as in Example 1, the reaction was performed using 36.2 g (0.2 mol) of the above-produced 2-bromo-4-butyrothiolactone, and the reaction solution after the reaction was subjected to the pH adjustment, suction-filtration and extraction operations in the same manner as in Example 1, followed by the distillation-purification of the objective compound to obtain 21.4 g of 2-mercapto-4-butyrothiolactone (having a boiling point of 62° C./0.2 kPa; with a yield of 80%). The pH of the reaction solution was within the range of 7.5 to 8.9 from when the dropwise addition of 2-bromo-4-butyrothiolactone was initiated to the stirring after the dropwise addition was completed.

Example 5

Production of 2-mercapto-6-hexanolactam (1) Production of 2-bromo-6-hexanolactam A benzene (50 g; manufactured by JUNSEI CHEMICAL Co., Ltd.) solution in which 240 g (1.5 mol) of bromine (manufactured by JUNSEI CHEMICAL Co., Ltd.) were dissolved was cooled with ice to 10° C. To the cooled solution, 450 g (1.6 mol) of 90% phosphorus tribromide (manufactured by Wako Pure Chemical Industries Ltd.) were added while the temperature of the reaction solution was maintained at 10° C. or less, and the resultant reaction solution was stirred for 60 minutes. Into the reaction solution, a benzene (220 g) solution in which 85 g (0.75 mol) of commercially available 6-hexanolactam (trade name: ε-caprolactam; manufactured by Tokyo Chemical Industry Co., Ltd.) were dissolved was added dropwise through a dropping funnel over 30 minutes while maintaining the temperature of the reaction solution at 10° C. or less.

After the completion of the dropwise addition, the reaction solution was heated up to 45° C. and stirred for 5.5 hours. The reaction solution after the reaction was poured into 1000 g of ice and the resultant benzene phase was recovered by separating the phases. The recovered benzene phase was concentrated under a reduced pressure to give 53.5 g of a crude crystal of 2-bromo-6-hexanolactam.

(2) Production of 2-mercapto-6-hexanolactam

In substantially the same manner as in Example 1, the reaction was performed using 39 g of the above-produced crude crystal of 2-bromo-6-hexanolactam and the reaction solution after the reaction was subjected to the pH adjustment, suction-filtration and extraction operations in the same manner as in Example 1, followed by concentration in which the volume of the reaction solution was reduced to approximately the half under a reduced pressure. To the concentrated reaction solution, 330 g of ethyl acetate (GUARANTEED REAGENT, manufactured by JUNSEI CHEMICAL Co., Ltd.) were added to extract the reaction solution. The resultant aqueous phase was reextracted with 330 g of ethyl acetate. These extracted organic phases were combined and concentrated under a reduced pressure to give a crude crystal of 2-mercapto-6-hexanolactam. The obtained crude crystal of 2-mercapto-6-hexanolactam was separation-purified by silica gel column chromatography in which the mobile phase was a mixed vehicle of hexane and ethyl acetate (the volume ratio of hexane:ethyl acetate was 2:1). Consequently, 26.1 g (0.18 mol) of a crystal of 2-mercapto-6-hexanolactam (with a yield of 24% from 6-hexanolactam) were obtained. The pH of the reaction solution was within the range of 7.6 to 8.9 from when the dropwise addition of 2-bromo-6-hexanolactam was initiated to the stirring after the dropwise addition was completed.

Example 6

Synthesis of N-methyl-2-mercapto-4-butyrolactam (1) Production of 2,4-dibromobutyric acid bromide 2,4-dibromobutyric acid bromide was synthesized from 4-butyrolactone by the following method similar to the method of A. Kamal et. al. (Tetrahedron Asymmetry 2003, 14, 2587-2594).

To 100 g (1.15 mol) of 4-butyrolactone (manufactured by Tokyo Chemical Industry Co., Ltd.), 12.5 g (0.046 mol) of phosphorus tribromide (manufactured by Tokyo Chemical Industry Co., Ltd.) was added to produce a solution.

Into the above-obtained solution, 200 g (1.25 mol) of bromine (manufactured by Wako Pure Chemical Industries Ltd.) were added dropwise over approximately 2 hours, while maintaining the temperature of the solution at approximately 10° C. or less and stirring the solution. After the completion of the dropwise addition, the temperature of the resultant reaction solution was elevated to 70° C. and 200 g (1.25 mol) of bromine (manufactured by Wako Pure Chemical Industries Ltd.) were added dropwise thereinto over approximately 30 minutes. The temperature of the reaction solution after the completion of the dropwise addition was elevated to 80° C. and the reaction solution was stirred at 80° C. for 3 hours.

After the completion of the reaction, a glass tube was inserted into the reaction solution, and nitrogen was blown into the reaction solution through the glass tube, to thereby remove unreacted bromine and hydrogen bromide generated by the reaction. The resultant reaction solution was distilled under a reduced pressure to give 190 g (0.61 mol) of 2,4-dibromobutyric acid bromide (having a boiling point of 87 to 88° C./0.7 kPa; with a yield of 53%).

(2) Synthesis of N-methyl-2-bromo-4-butyrolactam

N-methyl-2-bromo-4-butyrolactam was synthesized from 2,4-dibromobutyric acid bromide by the following method similar to the method of A. Kamal et. al. (Tetrahedron Asymmetry 2003, 14, 2587-2594).

A solution mixture of 31.6 g (0.4 mol) of 40% methylamine aqueous solution (manufactured by JUNSEI CHEMICAL Co., Ltd.) and 13.2 g of water was cooled to 10° C. or less. While the solution mixture was maintained at 10° C. or less, 148 g (0.48 mol) of 2,4-dibromobutyric acid bromide were added dropwise into the solution mixture over 15 minutes. After the completion of the dropwise addition, the temperature of the resultant reaction solution was elevated to 30° C. and the reaction solution was stirred for 30 minutes. To the reaction solution, 200 g of chloroform were added to extract the organic phase. The organic phase was separated and was dried by adding magnesium sulfate thereto.

The organic phase from which the magnesium sulfate was filtered off was concentrated to give a crude crystal. The crude crystal was washed with a 1:1 solution mixture of diethyl ether:hexane to produce 85.6 g (0.33 mol) of N-methyl-2,4-dibromobutyric acid amide (having a melting point of 54° C.;

with a yield of 69%). The obtained crystal was dissolved in 720 g of THF (Guaranteed Reagent; manufactured by JUNSEI CHEMICAL Co., Ltd.).

The resultant solution was cooled with ice to 10° C. or less and 26.4 g (0.66 mol) of 60% NaH in mineral oil (manufactured by JUNSEI CHEMICAL Co., Ltd.) were gradually added thereto over approximately 15 minutes. After the completion of the addition, the temperature of the resultant reaction solution was elevated to room temperature and the reaction solution was stirred for 2 hours. The reaction solution after the reaction was concentrated to approximately one third of the original weight, and the concentrate was introduced into 400 g of an ice-water mixture. The resultant solution mixture was extracted with 400 g of chloroform. The resultant chloroform phase was concentrated, and the concentrate was purified by silica gel column chromatography to give 45.6 g (0.25 mol) of N-methyl-2-bromo-4-butyrolactam (with a yield of 77%).

(3) Synthesis of N-methyl-2-mercapto-4-butyrolactam 19.1 g (0.24 mol) of 70% sodium hydrosulfide (manufactured by JUNSEI CHEMICAL Co., Ltd.) were dissolved in a solvent mixture of 13.1 g of 1,2-dimethoxyethane (Guaranteed Reagent; manufactured by JUNSEI CHEMICAL Co., Ltd.) with 13.1 g of purified water (which had been distilled and passed through an ion exchange filter) at room temperature. While the resultant solution was cooled with ice (to 10° C. or less) and under normal pressure (about 0.10 MPa), 8.8 g of hydrochloric acid (GUARANTEED REAGENT, 35% to 37%; manufactured by JUNSEI CHEMICAL Co., Ltd.) were added with stirring the solution to adjust the pH of the solution to 8.9, and the temperature of the solution was cooled with ice to 10° C. or less. While cooling the solution to maintain the temperature of the solution at 10° C. or less, a solution mixture of 35.6 g (0.2 mol) of N-methyl-2-bromo-4-butyrolactam and 156 g of DMF was added dropwise into the solution over approximately 30 minutes. The reaction solution after the completion of the dropwise addition was stirred for 5 minutes. The pH of the reaction solution was within the range of 7.6 to 8.9 from when the dropwise addition of N-methyl-2-bromo-4-butyrolactam was initiated to the stirring after the dropwise addition was completed.

Thereafter, while cooling the solution to 10° C. or less, 8.8 g of hydrochloric acid were added to the solution over approximately 2 minutes to adjust the pH of the solution at 6.0. An inorganic salt deposited in the solution was removed by suction-filtration, and 310 g of ethyl acetate (Guaranteed Reagent; manufactured by JUNSEI CHEMICAL Co., Ltd.) were added to the resultant filtrate to extract the organic phase. The resultant aqueous phase was reextracted with 550 g of ethyl acetate. These extracted organic phases were combined and the resultant organic phase was concentrated under a reduced pressure. The concentrate was purified by silica gel column chromatography to give 20.6 g (0.157 mol) of N-methyl-2-mercapto-4-butyrolactam (with a yield of 78%).

Example 7

Synthesis of 2-mercapto-4-butyrolactam (1) Synthesis of 2-bromo-4-butyrolactam

In substantially the same manner as in Example 6 except that 2,4-dibromobutyric acid bromide obtained by the method described in Example 6 was used and that aqueous ammonia was used instead of 40% methylamine aqueous solution, 73.5 g (0.30 mol) of 2,4-dibromobutyric acid amide (having a melting point of 79° C.; with a yield of 63%) was obtained as a crystal. The obtained crystal was dissolved in 650 g of THF (Guaranteed Reagent; manufactured by JUNSEI CHEMICAL Co., Ltd.). The resultant solution was cooled with ice to 10° C. or less and thereto, 24 g (0.60 mol) of 60% NaH in mineral oil (manufactured by JUNSEI CHEMICAL Co., Ltd.) were gradually added over approximately 15 minutes. After the completion of the addition, the temperature of the resultant reaction solution was elevated to room temperature and the reaction solution was stirred for 2 hours. The reaction solution after the reaction was evaporated and concentrated to approximately one third of the original weight, and the concentrate was introduced into 360 g of an ice-water mixture. The resultant solution mixture was extracted with 360 g of chloroform. The resultant chloroform phase was evaporated and concentrated, and the concentrate was purified by silica gel column chromatography to give 37.9 g (0.23 mol) of 2-bromo-4-butyrolactam (with a yield of 27%).

(2) Synthesis of 2-mercapto-4-butyrolactam

In substantially the same manner as in Example 6 except that 32.8 g (0.2 mol) of 2-bromo-4-butyrolactam were used instead of N-methyl-2-bromo-4-butyrolactam, 18.1 g (0.15 mol) of 2-mercapto-4-butyrolactam were synthesized (with a yield of 77%) The pH of the reaction solution was within the range of 7.6 to 8.9 from when the dropwise addition of 2-bromo-4-butyrolactam was initiated to the stirring after the dropwise addition was completed.

Example 8

Synthesis of N-ethyl-2-mercapto-4-butyrolactam (1) Synthesis of N-ethyl-2-bromo-4-butyrolactam In substantially the same manner as in Example 6 except that 2,4-dibromobutyric acid bromide obtained by the method described in Example 6 was used and that 70% ethylamine aqueous solution was used instead of 40% methylamine aqueous solution, 91.7 g (0.336 mol) of N-ethyl-2,4-dibromobutyric acid amide was obtained (with a yield of 70%). In substantially the same manner as in Example 7, the reaction was performed using 81.9 g (0.30 mol) of the above-obtained N-ethyl-2,4-dibromobutyric acid amide. Consequently, 40.9 g (0.21 mol) of N-ethyl-2-bromo-4-butyrolactam was obtained (with a yield of 71%).

(2) Synthesis of N-ethyl-2-mercapto-4-butyrolactam

In substantially the same manner as in Example 6 except that 38.4 g (0.2 mol) of N-ethyl-2-bromo-4-butyrolactam was used instead of N-methyl-2-bromo-4-butyrolactam, 23.8 g (0.16 mol) of N-ethyl-2-mercapto-4-butyrolactam were synthesized (with a yield of 82%). The pH of the reaction solution was within the range of 7.5 to 8.9 from when the dropwise addition of N-ethyl-2-bromo-4-butyrolactam was initiated to the stirring after the dropwise addition was completed.

Example 9

Synthesis of N-methoxy-2-mercapto-4-butyrolactam (1) Synthesis of N-methoxy-2-bromo-4-butyrolactam N-methoxy-2-bromo-4-butyrolactam was synthesized using 2,4-dibromobutyric acid bromide by the following method similar to the method of Ikuta et. al. (Journal of Medicinal Chemistry 1987, 30, 1995-1998).

52 g (0.62 mol) of O-methylhydroxy amine hydrochloride (manufactured by JUNSEI CHEMICAL Co., Ltd.), 100 g of purified water (which had been distilled and passed through an ion exchange filter) and 500 mL of chloroform (Guaranteed Reagent; manufactured by JUNSEI CHEMICAL Co., Ltd.) were mixed by stirring under a condition of cooling with ice. To the resultant mixture, a solution mixture of 169 g (0.55 mol) of 2,4-dibromobutyric acid bromide and 100 mL of chloroform was added. Into the resultant mixture, 100 mL of an aqueous solution in which 50 g of NaOH were dissolved were added dropwise while cooling the reaction solution so that the reaction temperature was 10° C. or less.

After the completion of the dropwise addition, the resultant chloroform phase of the reaction solution was separated and was washed with 0.5N hydrochloric acid, a saturated aqueous sodium hydrogencarbonate solution and a saturated saline in this order, followed by drying the phase by magnesium sulfate. This resultant solution was concentrated under a reduced pressure to produce 130 g of oil containing N-methoxy-2,4-dibromobutyric acid amide. The oil was subjected to the next reaction without particular purification.

130 g of the above-obtained oil containing N-methoxy-2,4-dibromobutyric acid amide were dissolved in 500 mL of benzene. To the resultant solution, 12 g of sodium hydride were gradually added while cooling the solution to 15° C. to 20° C. After the completion of the addition, ice was added to the resultant reaction solution to decompose excessive sodium hydride. The resultant solution was washed with a saturated saline, followed by drying the solution by magnesium sulfate. The solution was concentrated under a reduced pressure and purified by silica gel-acetone/benzene column chromatography. Consequently, 39 g (0.2 mol) of N-methoxy-2-bromo-4-butyrolactam (with a yield of 36% from 2,4-dibromobutyric acid bromide) was obtained.

(2) Synthesis of
N-methoxy-2-mercapto-4-butyrolactam

In substantially the same manner as in Example 6 except that 39 g (0.2 mol) of N-methoxy-2-bromo-4-butyrolactam were used instead of N-methyl-2-bromo-4-butyrolactam, 23.8 g (0.16 mol) of N-methoxy-2-mercapto-4-butyrolactam were synthesized (with a yield of 81%). The pH of the reaction solution was within the range of 7.5 to 8.9 from when the dropwise addition of N-methoxy-2-bromo-4-butyrolactam was initiated to the stirring after the dropwise addition was completed.

Example 10

Synthesis of N-ethoxy-2-mercapto-4-butyrolactam (1) Synthesis of N-ethoxy-2-bromo-4-butyrolactam In substantially the same manner as in Example 9 except that 169 g (0.55 mol) of 2,4-dibromobutyric acid bromide obtained by the method described in Example 6 were used and that 61 g (0.62 mol) of O-ethylhydroxy amine hydrochloride (manufactured by Wako Pure Chemical Industries Ltd.) were used instead of O-methylhydroxy amine hydrochloride, 137 g of oil containing N-ethoxy-2,4-dibromobutyric acid amide were obtained. The oil was subjected to the next reaction without particular purification.

137 g of the above-obtained oil containing N-ethoxy-2,4-dibromobutyric acid amide were dissolved in 500 mL of benzene. To the resultant solution, 12 g of sodium hydride were gradually added while cooling the solution to 15° C. to 20° C. After the completion of the addition, ice was added to the resultant reaction solution to decompose excessive sodium hydride. The resultant solution was washed with a saturated saline, followed by drying the solution by magnesium sulfate. The solution was concentrated under a reduced pressure and purified by silica gel-acetone/benzene column chromatography to give 42 g (0.20 mol) of N-ethoxy-2-bromo-4-butyrolactam (with a yield of 37% from 2,4-dibromobutyric acid bromide).

(2) Synthesis of
N-ethoxy-2-mercapto-4-butyrolactam

In substantially the same manner as in Example 6 except that 42 g (0.2 mol) of N-ethoxy-2-bromo-4-butyrolactam were used instead of N-methyl-2-bromo-4-butyrolactam, 24.8 g (0.15 mol) of N-ethoxy-2-mercapto-4-butyrolactam were synthesized (with a yield of 77%). The pH of the reaction solution was within the range of 7.6 to 8.9 from when the dropwise addition of N-ethoxy-2-mercapto-4-butyrolactam was initiated to the stirring after the dropwise addition was completed.

Examples 11 to 15

In substantially the same manner as in Example 1 except that the reaction was performed while the pH of the sodium hydrosulfide solution was preliminarily adjusted as described in Table 1, 2-mercapto-4-butyrolactone was synthesized. The results are shown in Table 1. The conversion, SH selectivity, MS selectivity and DS selectivity in Table 1 were calculated from the HPLC analysis results.

Comparative Examples 1 and 2

In substantially the same manner as in Example 1 except that the reaction was performed while the pH of the sodium hydrosulfide solution was preliminarily adjusted to 6.5 or 13.0, 2-mercapto-4-butyrolactone was synthesized. The results are shown in Table 1. The conversion, SH selectivity, MS selectivity and DS selectivity in Table 1 were calculated from the HPLC analysis results.

Comparative Example 3

A sodium hydrosulfide solution was prepared according to the method described in Example 1 without the pH adjustment with hydrochloric acid. The pH of the solution was 14.0. Using the solution, 2-mercapto-4-butyrolactone was synthesized in substantially the same manner as in Example 1. The results are shown in Table 1. The conversion, SH selectivity, MS selectivity and DS selectivity in Table 1 were calculated from the HPLC analysis results.

TABLE 1

| | Examples | | | | | Comparative Examples | | |
|---|---|---|---|---|---|---|---|---|
| | 11 | 12 | 13 | 14 | 15 | 1 | 2 | 3 |
| pH of NaSH solution | 8.0 | 8.5 | 9.0 | 9.5 | 10.0 | 6.5 | 13.0 | 14.0 |
| pH during the reaction | 7.0~8.0 | 7.2~8.5 | 7.4~9.0 | 7.5~9.5 | 7.8~10.0 | 6.0~6.5 | 11.0~13.0 | 11.0~14.0 |
| Conversion | 100% | 100% | 100% | 100% | 100% | 13% | 100% | 100% |
| SH selectivity | 86% | 89% | 89% | 88% | 85% | 3% | 61% | 32% |
| MS selectivity | 8% | 4% | 4% | 5% | 9% | 6% | 21% | 61% |
| DS selectivity | 4% | 5% | 6% | 5% | 5% | 4% | 6% | 6% |

Abbreviation:
SH = 2-mercapto-4-butyrolactone
MS = Monosulfide represented by the following Formula (A) (n = 1).
DS = Disulfide represented by the following Formula (A) (n = 2).
(A)

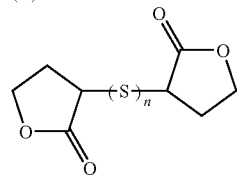

Examples 16 to 21

In substantially the same manner as in Example 1 except that the pH of the sodium hydrosulfide solution before the reaction was adjusted to 8.5 and that the equivalent ratio of the metal sulfide or metal hydrosulfide to 2-bromo-4-butyrolactone was changed as described in Table 2, the reaction was performed to synthesize 2-mercapto-4-butyrolactone. The results are shown in Table 2. The conversion, SH selectivity, MS selectivity and DS selectivity in Table 2 were calculated from the HPLC analysis results. The pH of the reaction solution was within the range of 7.0 to 11.0 from when the dropwise addition of 2-bromo-4-butyrolactone was initiated to the stirring after the dropwise addition was completed.

TABLE 2

| | Examples | | | | | |
|---|---|---|---|---|---|---|
| | 16 | 17 | 18 | 19 | 20 | 21 |
| Equivalent ratio of sodium hydrosulfide to halogenoheterocyclic compound | 1.0 | 1.5 | 2.0 | 3.0 | 5.0 | 7.0 |
| Conversion | 100% | 100% | 100% | 100% | 100% | 100% |
| SH selectivity | 70% | 74% | 82% | 89% | 95% | 95% |
| MS selectivity | 20% | 18% | 10% | 4% | 1% | 0% |
| DS selectivity | 7% | 7% | 6% | 5% | 4% | 5% |

Abbreviation:
SH = 2-mercapto-4-butyrolactone
MS = Monosulfide represented by the above-mentioned Formula (A) (n = 1).
DS = Disulfide represented by the above-mentioned Formula (A) (n = 2).

Examples 22 to 32

For the screening of solvents, Examples 22 to 32 were performed. In these Examples, the molar ratio of sodium hydrosulfide to 2-bromo-4-butyrolactone and the pH of the sodium hydrosulfide solution just before the reaction were fixed at 1:1 and 11.0 respectively to clarify the difference in effects among the solvents. Specifically, Examples were performed according to the following procedures.

18 g (0.22 mol) of 70% sodium hydrosulfide (manufactured by JUNSEI CHEMICAL Co., Ltd.) were added to 68 g of an organic solvent (Guaranteed Reagent; manufactured by JUNSEI CHEMICAL Co, Ltd.) shown in Table 3, or 68 g of purified water (which had been distilled and passed through an ion exchange filter), or a mixed solvent of 34 g of an organic solvent (Guaranteed Reagent; manufactured by JUNSEI CHEMICAL Co., Ltd.) above and 34 g of purified water (which had been distilled and passed through an ion exchange filter). The compound was dissolved at room temperature.

While the resultant solution was cooled with ice (to 10° C. or less) and under normal pressure (about 0.10 MPa), hydrochloric acid was added with stirring the solution to adjust the pH of the solution to 11.0, and the temperature of the solution was cooled with ice to 10° C. or less.

Then, while cooling the solution so as to maintain the temperature of the solution at 10° C. or less, 34 g (0.2 mol) of 2-bromo-4-butyrolactone (manufactured by Tokyo Chemical Industry Co., Ltd.) were added dropwise into the solution over approximately 20 minutes. In every example, the pH of the reaction solution was within the range of 7.0 to 11.0 from when the dropwise addition of 2-bromo-4-butyrolactone was initiated to the stirring after the dropwise addition was completed.

The results obtained using different solvents are shown in Table 3. The SH selectivity and MS selectivity shown in Table 3 were calculated from the HPLC results.

TABLE 3

| Examples | | Reaction solvent | Conversion | SH selectivity | MS selectivity |
|---|---|---|---|---|---|
| 22 | Single | Water single solvent | 100% | 28% | 65% |
| 23 | solvent | Methanol single solvent | 100% | 29% | 66% |
| 24 | | Dimethylformamide single solvent | 100% | 32% | 64% |
| 25 | | Propylene glycol single solvent | 100% | 34% | 59% |
| 26 | | 50% methylethyl ketone aqueous solution (ununiform) | 100% | 28% | 70% |
| 27 | 50% | 50% methanol aqueous solution | 100% | 50% | 42% |
| 28 | aqueous | 50% N-methylpyrrolidone aqueous solution | 100% | 52% | 41% |
| 29 | solution | 50% acetone aqueous solution | 100% | 56% | 34% |
| 30 | | 50% dimethylformamide aqueous solution | 100% | 56% | 37% |
| 31 | | 50% 1,4-dioxane aqueous solution | 100% | 57% | 33% |
| 32 | | 50% 1,2-dimethoxyethane aqueous solution | 100% | 60% | 32% |

Abbreviation:
SH = 2-mercapto-4-butyrolactone
MS = Monosulfide represented by the above-mentioned Formula (A) (n = 1)

Examples 33 to 36

In substantially the same manner as in Example 1 except that the temperature of the reaction solution during the reaction was changed as described in Table 4, the reaction was performed to synthesize 2-mercapto-4-butyrolactone. The results are shown in Table 4. The SH reaction yields in Table 4 were calculated from the HPLC analysis results of samples which had been picked up from the reaction solution when the pH of the reaction solution was adjusted to 4.0.

TABLE 4

| | Temperature of reaction solution | SH reaction yield |
|---|---|---|
| Example 33 | 5° C. or less | 90% |
| Example 34 | 10° C. | 89% |
| Example 35 | 30° C. | 70% |
| Example 36 | 50° C. | 46% |

Abbreviation:
SH = 2-mercapto-4-butyrolactone

Examples 37 to 41

In the same manner as in Example 1, 2-mercapto-4-butyrolactone was synthesized. After the reaction, the pH of the reaction solution was adjusted as shown in Table 5. The resultant solution was stored at 25° C. or 50° C. for 3 hours, and the storage stability of SH (2-mercapto-4-butyrolactone) was evaluated. The SH storage stability is shown as a percentage (%) of the SH concentration determined after the storage, relative to the SH concentration immediately after the pH adjustment (100%). The SH concentrations were measured by HPLC.

The results are shown in Table 5.

TABLE 5

| | Examples | | | | |
|---|---|---|---|---|---|
| | 37 | 38 | 39 | 40 | 41 |
| pH of the reaction solution after the reaction | 2.0 | 4.0 | 6.0 | 1.0 | 8.0 |
| Storage temperature 25° C. | 98% | 100% | 99% | 93% | 90% |
| Storage temperature 50° C. | 79% | 100% | 98% | 51% | 72% |

TABLE 5-continued

| | Examples | | | | |
|---|---|---|---|---|---|
| | 37 | 38 | 39 | 40 | 41 |

Abbreviation:
SH = 2-mercapto-4-butyrolactone

The results in Table 5 show that the decomposition of SH are suppressed in solutions which are pH adjusted to 2.0 to 6.0 after the reaction.

Example 42

Production of 2-mercapto-4-butyrolactone (using Na$_2$S)

144 g (0.6 mol) of sodium sulfide nonahydrate (manufactured by JUNSEI CHEMICAL Co., Ltd.) were dissolved in a mixed solvent of 34 g of 1,2-dimethoxyethane (Guaranteed Reagent; manufactured by JUNSEI CHEMICAL Co., Ltd.) and 34 g of purified water (which had been distilled and passed through an ion exchange filter) at room temperature. While the resultant solution was cooled with ice (to 10° C. or less) and under normal pressure (about 0.10 MPa), 79 g of hydrochloric acid (GUARANTEED REAGENT, 35% to 37%; manufactured by JUNSEI CHEMICAL Co., Ltd.) were added with stirring the solution to adjust the pH of the solution to 8.9. While cooling the solution to maintain the temperature of the solution at 10° C. or less, 34 g (0.2 mol) of 2-bromo-4-butyrolactone (manufactured by Tokyo Chemical Industry Co., Ltd.) were added dropwise into the solution over approximately 20 minutes. The reaction solution after the completion of the dropwise addition was stirred for 2 minutes. The pH of the reaction solution was within the range of 7.5 to 8.9 from when the dropwise addition of 2-bromo-4-butyrolactone was initiated to the stirring after the dropwise addition was completed.

Thereafter, while cooling the solution to 10° C. or less, 24 g of hydrochloric acid were added to the solution over approximately 5 minutes to adjust the pH of the solution to 4.0. An inorganic salt deposited in the solution was removed by suction-filtration, and 20 g of ethyl acetate (Guaranteed Reagent; manufactured by JUNSEI CHEMICAL Co., Ltd.) were added to the resultant filtrate to extract the organic phase. The resultant aqueous phase was reextracted with 34 g of ethyl acetate. These extracted organic phases were combined and the resultant organic phase was concentrated and purified by distillation under a reduced pressure to give 17 g of 2-mercapto-4-butyrolactone (having a boiling point of 94° C./0.3 kPa; with a yield of 72%).

Example 43

Production of 2-mercapto-4-butyrolactone (using CaS)

43.3 g (0.6 mol) of calcium sulfide (manufactured by SIGMA-ALDRICH Corporation) were dissolved in a mixed solvent of 34 g of 1,2-dimethoxyethane (Guaranteed Reagent; manufactured by JUNSEI CHEMICAL Co., Ltd.) and 34 g of purified water (which had been distilled and passed through an ion exchange filter) at room temperature. While the resultant solution was cooled with ice (to 10° C. or less) and under normal pressure (about 0.10 MPa), 78 g of hydrochloric acid (GUARANTEED REAGENT, 35% to 37%; manufactured by JUNSEI CHEMICAL Co., Ltd.) were added with stirring the solution to adjust the pH of the solution to 8.9. While cooling the solution to maintain the temperature of the solution at 10° C. or less, 34 g (0.2 mol) of 2-bromo-4-butyrolactone (manufactured by Tokyo Chemical Industry Co., Ltd.) were added dropwise into the solution over approximately 20 minutes. The reaction solution after the completion of the dropwise addition was stirred for 2 minutes. The pH of the reaction solution was within the range of 7.5 to 8.9 from when the dropwise addition of 2-bromo-4-butyrolactone was initiated to the stirring after the dropwise addition was completed.

Thereafter, while cooling the solution to 10° C. or less, 24 g of hydrochloric acid were added to the solution over approximately 5 minutes to adjust the pH of the solution to 4.0. An inorganic salt precipitated in the solution was removed by suction-filtration, and 20 g of ethyl acetate (Guaranteed Reagent; manufactured by JUNSEI CHEMICAL Co., Ltd.) were added to the resultant filtrate to extract the organic phase. The resultant aqueous phase was reextracted with 34 g of ethyl acetate. These extracted organic phases were combined and the resultant organic phase was concentrated and purified by distillation under a reduced pressure to give 15 g of 2-mercapto-4-butyrolactone (having a boiling point of 94° C./0.3 kPa; with a yield of 63%).

The invention claimed is:

1. A method for producing a mercapto lactone, mercapto thiolactone or mercapto lactam represented by Formula (1):

(1)

wherein X represents any structure of —O—, —S—, —NH—, and —NR$^1$—; R$^1$ represents any of an alkyl group, alkoxy group and alkoxyalkyl group each having 1 to 6 carbon atoms; and Z$^1$ represents an alkylene group having one mercapto group and the mercapto group is directly bound to the carbon atom adjacent to the carbonyl carbon in the compound represented by Formula (1), the method comprising reacting a metal sulfide or a metal hydrosulfide with a compound represented by Formula (2) in the presence of a solvent at a pH of 7.0 to 11.0:

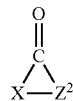

(2)

wherein X is as defined in Formula (1); and Z$^2$ represents an alkylene group having one halogen group and the halogen group is directly bound to the carbon atom adjacent to the carbonyl carbon in the compound represented by Formula (2).

2. The method for producing a mercapto lactone, mercapto thiolactone or mercapto lactam according to claim 1, wherein the compound represented by Formula (1) is selected from the group consisting of 2-mercapto-4-butyrolactone (2-mercapto-4-butanolide), 2-mercapto-4-methyl-4-butyrolactone, 2-mercapto-4-ethyl-4-butyrolactone, 2-mercapto-4-butyrothiolactone, 2-mercapto-4-butyrolactam, N-methoxy-2-mercapto-4-butyrolactam, N-ethoxy-2-mercapto-4-butyrolactam, N-methyl-2-mercapto-4-butyrolactam, N-ethyl-2-mercapto-4-butyrolactam, N-(2-methoxy)ethyl-2-mercapto-4-butyrolactam, N-(2-ethoxy)ethyl-2-mercapto-4-butyrolactam, 2-mercapto-5-valerolactone, 2-mercapto-5-valerolactam, N-methyl-2-mercapto-5-valerolactam, N-ethyl-2-mercapto-5-valerolactam, N-(2-methoxy)ethyl-2-mercapto-5-valerolactam, N-(2-ethoxy)ethyl-2-mercapto-5-valerolactam, and 2-mercapto-6-hexanolactam.

3. The method for producing a mercapto lactone, mercapto thiolactone or mercapto lactam according to claim 1, wherein the metal sulfide is an alkali metal sulfide, an alkaline earth metal sulfide or a mixture thereof.

4. The method for producing a mercapto lactone, mercapto thiolactone or mercapto lactam according to claim 1, wherein the metal sulfide is at least one compound selected from the group consisting of sodium sulfide, potassium sulfide, calcium sulfide and magnesium sulfide.

5. The method for producing a mercapto lactone, mercapto thiolactone or mercapto lactam according to claim 1, wherein the metal hydrosulfide is sodium hydrosulfide or potassium hydrosulfide.

6. The method for producing a mercapto lactone, mercapto thiolactone or mercapto lactam according to claim 1, wherein the solvent is a mixed solvent of water and an organic solvent in which the water:organic solvent weight ratio is 1:0.1-10.

7. The method for producing a mercapto lactone, mercapto thiolactone or mercapto lactam according to claim 6, wherein the organic solvent is one or more solvents selected from the group consisting of methanol, N-methylpyrrolidone, acetone, 1,4-dioxane, 1,2-dimethoxyethane and N,N-dimethylformamide.

8. The method for producing a mercapto lactone, mercapto thiolactone or mercapto lactam according to claim 1, wherein the pH is maintained in the aforementioned range by adding an inorganic acid or an inorganic alkali to the reaction solution from the start of the reaction to the completion of the reaction.

9. The method for producing a mercapto lactone, mercapto thiolactone or mercapto lactam according to claim 1, wherein the reaction is performed at not more than 40° C.

10. The method for producing a mercapto lactone, mercapto thiolactone or mercapto lactam according to claim 1, wherein the reaction is performed by dissolving or dispersing the metal sulfide or the metal hydrosulfide in the solvent and adding the compound represented by Formula (2) to the resultant solution or slurry while controlling the temperature of the solution or slurry in the range of −20 to 40° C.

11. The method for producing a mercapto lactone, mercapto thiolactone or mercapto lactam according to claim 1, wherein the reaction is performed by dissolving or dispersing the metal sulfide or the metal hydrosulfide in the solvent; adjusting the pH of the resultant solution or slurry in the range of 7.5 to 11.0; and adding the compound represented by Formula (2) to the solution or slurry.

12. The method for producing a mercapto lactone, mercapto thiolactone or mercapto lactam according to claim 11, wherein the pH of the solution or slurry of the metal sulfide or the metal hydrosulfide is achieved by adding an inorganic acid to the solution or slurry while controlling the temperature of the solution or slurry at not more than 40° C.

13. The method for producing a mercapto lactone, mercapto thiolactone or mercapto lactam according to claim 1, wherein the equivalent ratio of the compound represented by Formula (2) to the metal sulfide or the metal hydrosulfide is 1:0.8-5.0.

14. The method for producing a mercapto lactone, mercapto thiolactone or mercapto lactam according to claim 1, further comprising adjusting the pH of the reaction solution in the range of 2.0 to 6.0 after the completion of the reaction.

15. The method for producing a mercapto lactone, mercapto thiolactone or mercapto lactam according to claim 14, wherein the pH of the reaction solution after the reaction is achieved by adding an inorganic acid thereto after the completion of the reaction.

* * * * *